(12) United States Patent
Cully et al.

(10) Patent No.: US 9,107,733 B2
(45) Date of Patent: Aug. 18, 2015

(54) REMOVABLE BLOOD CONDUIT FILTER

(75) Inventors: Edward H Cully, Flagstaff, AZ (US);
Cody L. Hartman, Flagstaff, AZ (US);
Craig T. Nordhausen, Parker, CO (US);
Eric M. Tittelbaugh, Flagstaff, AZ (US); Michael J. Vonesh, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 1160 days.

(21) Appl. No.: 11/331,754

(22) Filed: Jan. 13, 2006

(65) Prior Publication Data
US 2007/0167974 A1 Jul. 19, 2007

(51) Int. Cl.
*A61M 29/00* (2006.01)
*A61F 2/01* (2006.01)
*A61B 17/221* (2006.01)
*A61B 17/22* (2006.01)
*A61F 2/06* (2013.01)

(52) U.S. Cl.
CPC ............... *A61F 2/01* (2013.01); *A61B 17/221* (2013.01); *A61B 2017/2212* (2013.01); *A61B 2017/22035* (2013.01); *A61F 2002/011* (2013.01); *A61F 2002/016* (2013.01); *A61F 2002/068* (2013.01); *A61F 2230/005* (2013.01); *A61F 2230/0006* (2013.01); *A61F 2230/008* (2013.01); *A61F 2230/0065* (2013.01); *A61F 2230/0093* (2013.01)

(58) Field of Classification Search
CPC ..... A61F 2/01; A61F 2002/011; A61F 2/013; A61F 2002/016; A61F 2002/018; A61F 2002/8486; A61F 2220/0025; A61F 2220/0091; A61F 2250/0037; A61F 2250/0039; A61F 2250/0063; A61F 2250/0064; A61F 2230/0067; A61F 2230/0076; A61F 2230/0086; A61F 2230/0093; A61F 2230/0095; A61F 2230/005; A61F 2230/008
USPC .......................................... 606/200, 159, 127
See application file for complete search history.

(56) References Cited

U.S. PATENT DOCUMENTS

| 751,918 A | 2/1904 | Jagger |
| 1,332,606 A | 3/1920 | Chuck |

(Continued)

FOREIGN PATENT DOCUMENTS

| EP | 0430848 | 6/1991 |
| EP | 1338250 | 8/2003 |

(Continued)

*Primary Examiner* — David Eastwood
*Assistant Examiner* — Erin Colello
(74) *Attorney, Agent, or Firm* — Wayne House 34623

(57) ABSTRACT

The present invention relates to a non-evertable blood filter that divides the transverse cross sectional area of a venous vessel into three annular regions or zones. The inner zone, the region immediately surrounding the longitudinal axis of the vessel, is maintained in a relatively open state with only minimal interference from the members making up the filter device so that blood flow can be maintained at a relatively normal rate. Concentrically surrounding the inner zone is the intermediate zone, to which captured emboli are directed out of the bloodstream passing primarily through the inner zone. Finally, concentrically surrounding the intermediate zone is the outer zone adjacent to the vessel wall. This is also intended to be kept free of emboli, so that emboli in the bloodstream immediately adjacent the vessel wall are directed away from the wall by the filter design and into the intermediate zone, thereby avoiding the accumulation of emboli adjacent the vessel wall that might otherwise result in stenosis. The blood filter is intended primarily for use as an inferior vena cava filter, although it can be made in a range of sizes allowing its use in blood vessels and particularly venous vessels of differing diameters. The filter is preferably removable.

11 Claims, 9 Drawing Sheets

(56) References Cited

U.S. PATENT DOCUMENTS

| | | | |
|---|---|---|---|
| 2,281,448 A | 4/1942 | Mathey | |
| 2,491,796 A | 12/1949 | Baume | |
| 2,767,703 A | 10/1956 | Nieburgs | |
| 2,893,563 A | 7/1959 | Bottum | |
| 3,137,298 A | 6/1964 | Glassman | |
| 3,334,629 A | 8/1967 | Cohn | |
| 3,540,431 A | 11/1970 | Mobin-Uddin | |
| 3,800,781 A | 4/1974 | Zalucki | |
| 3,868,956 A | 3/1975 | Alfidi et al. | |
| 3,952,747 A | 4/1976 | Kimmell, Jr. | |
| 4,403,612 A | 9/1983 | Fogarty | |
| 4,425,908 A | 1/1984 | Simon | |
| 4,494,531 A | 1/1985 | Gianturco | |
| 4,612,931 A * | 9/1986 | Dormia | 606/127 |
| 4,619,246 A * | 10/1986 | Molgaard-Nielsen et al. | 128/899 |
| 4,643,184 A | 2/1987 | Mobin-Uddin | |
| 4,665,906 A | 5/1987 | Jervis | |
| 4,680,029 A | 7/1987 | Ranford et al. | |
| 4,688,553 A | 8/1987 | Metals | |
| 4,727,873 A | 3/1988 | Mobin-Uddin | |
| 4,781,173 A | 11/1988 | Ven et al. | |
| 4,781,177 A * | 11/1988 | Lebigot | 128/897 |
| 4,793,348 A | 12/1988 | Palmaz | |
| 4,794,928 A | 1/1989 | Kletschka | |
| 4,817,600 A | 4/1989 | Herms et al. | |
| 4,832,055 A * | 5/1989 | Palestrant | 128/899 |
| 4,873,978 A | 10/1989 | Ginsburg | |
| 4,957,501 A | 9/1990 | Lahille et al. | |
| 4,969,891 A | 11/1990 | Gewertz | |
| 4,990,156 A | 2/1991 | Lefebvre | |
| 4,994,069 A | 2/1991 | Ritchart et al. | |
| 5,059,205 A | 10/1991 | El-Nounou et al. | |
| 5,067,957 A | 11/1991 | Jervis | |
| 5,102,415 A | 4/1992 | Guenther et al. | |
| 5,108,418 A | 4/1992 | Lefebvre | |
| 5,108,419 A | 4/1992 | Reger et al. | |
| 5,133,733 A | 7/1992 | Rasmussen et al. | |
| 5,147,379 A | 9/1992 | Sabbaghian et al. | |
| 5,152,777 A | 10/1992 | Goldberg et al. | |
| 5,160,342 A | 11/1992 | Reger et al. | |
| 5,190,546 A | 3/1993 | Jervis | |
| 5,234,458 A | 8/1993 | Metais | |
| 5,242,462 A | 9/1993 | El-Nounou et al. | |
| 5,344,427 A * | 9/1994 | Cottenceau et al. | 606/200 |
| 5,350,398 A | 9/1994 | Pavcnik et al. | |
| 5,370,657 A * | 12/1994 | Irie | 606/200 |
| 5,383,887 A | 1/1995 | Nadal | |
| 5,415,630 A | 5/1995 | Gory et al. | |
| 5,421,832 A | 6/1995 | Lefebvre | |
| 5,549,626 A | 8/1996 | Miller et al. | |
| 5,601,595 A * | 2/1997 | Smith | 606/200 |
| 5,626,605 A * | 5/1997 | Irie et al. | 623/1.1 |
| 5,634,942 A | 6/1997 | Chevillon et al. | |
| 5,649,906 A | 7/1997 | Gory et al. | |
| 5,649,953 A | 7/1997 | Lefebvre | |
| 5,669,933 A | 9/1997 | Simon et al. | |
| 5,681,347 A | 10/1997 | Cathcart et al. | |
| 5,683,411 A * | 11/1997 | Kavteladze et al. | 606/200 |
| 5,695,518 A | 12/1997 | Laerum | |
| 5,709,704 A | 1/1998 | Nott et al. | |
| 5,720,764 A | 2/1998 | Naderlinger | |
| 5,725,546 A | 3/1998 | Samson | |
| 5,725,550 A * | 3/1998 | Nadal | 606/200 |
| 5,746,767 A * | 5/1998 | Smith | 606/200 |
| 5,776,162 A | 7/1998 | Kleshinski | |
| 5,800,457 A | 9/1998 | Gelbfish | |
| 5,827,324 A * | 10/1998 | Cassell et al. | 606/200 |
| 5,836,968 A * | 11/1998 | Simon et al. | 606/200 |
| 5,836,969 A * | 11/1998 | Kim et al. | 606/200 |
| 5,853,420 A | 12/1998 | Chevillon et al. | |
| 5,893,869 A | 4/1999 | Barnhart et al. | |
| 5,928,261 A | 7/1999 | Ruiz | |
| 5,976,172 A * | 11/1999 | Homsma et al. | 606/200 |
| 5,984,947 A | 11/1999 | Smith | |
| 6,007,558 A | 12/1999 | Ravenscroft et al. | |
| 6,030,406 A * | 2/2000 | Davis et al. | 606/198 |
| 6,059,825 A | 5/2000 | Hobbs et al. | |
| 6,126,673 A * | 10/2000 | Kim et al. | 606/200 |
| 6,156,055 A | 12/2000 | Ravenscroft | |
| 6,187,017 B1 * | 2/2001 | Gregory, Jr. | 606/127 |
| 6,193,739 B1 | 2/2001 | Chevillon et al. | |
| 6,214,025 B1 * | 4/2001 | Thistle et al. | 606/200 |
| 6,245,087 B1 | 6/2001 | Addis | |
| 6,245,089 B1 | 6/2001 | Daniel et al. | |
| 6,258,026 B1 * | 7/2001 | Ravenscroft et al. | 600/200 |
| 6,267,776 B1 | 7/2001 | O'Connell | |
| 6,267,777 B1 | 7/2001 | Bosma et al. | |
| 6,273,900 B1 | 8/2001 | Nott et al. | |
| 6,306,163 B1 | 10/2001 | Jervis | |
| 6,306,163 B1 * | 10/2001 | Fitz | 623/1.12 |
| 6,361,545 B1 * | 3/2002 | Macoviak et al. | 606/200 |
| 6,368,338 B1 * | 4/2002 | Konya et al. | 606/200 |
| 6,391,044 B1 * | 5/2002 | Yadav et al. | 606/200 |
| 6,391,045 B1 * | 5/2002 | Kim et al. | 606/200 |
| 6,468,290 B1 | 10/2002 | Weldon et al. | |
| 6,511,496 B1 * | 1/2003 | Huter et al. | 606/200 |
| 6,511,503 B1 * | 1/2003 | Burkett et al. | 623/1.11 |
| 6,517,559 B1 | 2/2003 | O'Connell | |
| 6,635,070 B2 * | 10/2003 | Leeflang et al. | 606/200 |
| 6,660,021 B1 | 12/2003 | Palmer et al. | |
| 6,706,054 B2 | 3/2004 | Wessman et al. | |
| 6,783,538 B2 | 8/2004 | McGuckin, Jr. et al. | |
| 6,881,218 B2 * | 4/2005 | Beyer et al. | 606/200 |
| 6,949,103 B2 | 9/2005 | Mazzocchi et al. | |
| 6,958,074 B2 | 10/2005 | Russell | |
| 7,128,073 B1 * | 10/2006 | van der Burg et al. | 128/887 |
| 7,147,649 B2 * | 12/2006 | Thomas | 606/200 |
| 7,396,358 B2 * | 7/2008 | Appling et al. | 606/159 |
| 7,410,490 B2 * | 8/2008 | VanDusseldorp | 606/113 |
| 7,722,635 B2 * | 5/2010 | Beyer et al. | 606/200 |
| 7,799,049 B2 * | 9/2010 | Ostrovsky et al. | 606/200 |
| 8,025,668 B2 * | 9/2011 | McCartney | 606/106 |
| 8,267,954 B2 * | 9/2012 | Decant et al. | 606/200 |
| 8,409,241 B2 * | 4/2013 | Beyer et al. | 606/200 |
| 2001/0041899 A1 * | 11/2001 | Foster | 606/127 |
| 2002/0090388 A1 * | 7/2002 | Humes et al. | 424/422 |
| 2002/0161390 A1 * | 10/2002 | Mouw | 606/200 |
| 2002/0193828 A1 * | 12/2002 | Griffin et al. | 606/200 |
| 2003/0171774 A1 | 9/2003 | Freudenthal et al. | |
| 2003/0181942 A1 | 9/2003 | Sutton et al. | |
| 2003/0208253 A1 | 11/2003 | Beyer et al. | |
| 2004/0015224 A1 * | 1/2004 | Armstrong et al. | 623/1.12 |
| 2004/0088001 A1 * | 5/2004 | Bosma et al. | 606/200 |
| 2004/0138677 A1 * | 7/2004 | Little et al. | 606/127 |
| 2004/0199201 A1 * | 10/2004 | Kellett et al. | 606/200 |
| 2005/0043759 A1 | 2/2005 | Chanduszko | |
| 2005/0090858 A1 * | 4/2005 | Pavlovic | 606/200 |
| 2005/0209632 A1 * | 9/2005 | Wallace | 606/200 |
| 2005/0288703 A1 * | 12/2005 | Beyer et al. | 606/200 |
| 2005/0288704 A1 * | 12/2005 | Cartier et al. | 606/200 |
| 2006/0004402 A1 | 1/2006 | Voeller et al. | |
| 2006/0025852 A1 * | 2/2006 | Armstrong et al. | 623/1.17 |
| 2006/0041271 A1 * | 2/2006 | Bosma et al. | 606/200 |
| 2006/0079928 A1 * | 4/2006 | Cartier et al. | 606/200 |
| 2006/0241680 A1 * | 10/2006 | Johnson et al. | 606/200 |
| 2006/0247572 A1 * | 11/2006 | McCartney | 604/19 |
| 2006/0282113 A1 * | 12/2006 | Sater | 606/200 |
| 2007/0112372 A1 * | 5/2007 | Sosnowski et al. | 606/200 |
| 2007/0167974 A1 * | 7/2007 | Cully et al. | 606/200 |
| 2008/0188887 A1 * | 8/2008 | Batiste | 606/200 |
| 2009/0216263 A1 * | 8/2009 | Tekulve | 606/200 |

FOREIGN PATENT DOCUMENTS

| | | |
|---|---|---|
| FR | 2580504 | 10/1986 |
| GB | 2020557 | 5/1978 |
| WO | 98/23322 | 6/1998 |
| WO | 98/33443 | 8/1998 |
| WO | 01/45591 | 6/2001 |

\* cited by examiner

REMOVABLE BLOOD CONDUIT FILTER

FIELD OF THE INVENTION

This application relates to a blood conduit filter for capturing blood clots within a blood vessel, particularly within a venous vessel and still more particularly within the inferior vena cava.

BACKGROUND OF THE INVENTION

The migration of blood clot from the peripheral vasculature to the pulmonary arteries and lungs is known as pulmonary embolism. Typically, these clots originate in the lower limbs and migrate toward the heart and lungs. These clots can result from a variety of conditions such as trauma or deep vein thrombosis. If a clot is of sufficient size, it can occlude the pulmonary arteries and interfere with blood oxygenation in the lungs. This occlusion can result in shock or death. Individuals who experience a pulmonary embolism have a high likelihood of experiencing subsequent embolic events.

In these cases, blood thinning medications, e.g., anticoagulants such as heparin and warfarin sodium, or antiplatelet drugs such as aspirin, are given to the patient to prevent another embolic event. The utility of these medical therapies is limited because they may not be able to be administered to patients following surgery or stroke or for those patients presenting with a high risk of internal bleeding. Additionally, these medications are not always effective at preventing recurrent embolic events.

Therefore, surgical methods were developed in an effort to reduce the likelihood of pulmonary embolism recurrence by physically blocking the blood clot from migrating to the pulmonary artery and lungs. Since the inferior vena cava transports blood from the lower limbs to the heart, this vessel was a common site of surgical intervention. One method of treatment involved reducing the size of the inferior vena cava by application of ligatures or clips around the vessel. This prevented the migration of large clots from the lower vasculature to the heart. However, this required an extensive open surgical procedure with associated abdominal incision and general anesthesia. The effects of the surgical procedure coupled with lengthy recovery times led to complications such as vessel thrombosis and lower extremity swelling; thereby aggravating the condition of the patient.

To avoid this invasive surgical approach, less invasive catheter-based approaches have been developed. These involve the placement of filter devices in the inferior vena cava. These filters are inserted under local anesthesia through the femoral vein in the patient's leg, the right jugular vein in the patient's neck or the subclavian vein in the patient's arm. Using standard catheter techniques, the filters are then advanced intravascularly to the inferior vena cava where they are deployed and expanded against the vessel wall. These filters interrupt the migration of blood clots from the lower extremities to the heart and lungs. Once trapped in the filter, flow of blood around the clot helps to dissolve the embolic load in the device.

Previous filters take various forms. One type of filter is comprised of coiled or looped wires such as disclosed in U.S. Pat. Nos. 5,893,869 and 6,059,825. Another type of filter consists of legs with free ends having anchors for embedding and stabilizing in the vessel wall. Examples of these filters are disclosed in U.S. Pat. Nos. 4,688,553; 4,781,173; 4,832,055; 5,059,205; 5,984,947 and 6,007,558. Finally, filters that incorporate a means for removal are disclosed in U.S. Pat. Nos. 5,893,869; 5,984,947 and 6,783,538. U.S. Pat. No. 6,635,070 describes a temporary filter device that is removed by everting a portion of the filter structure to allow it to be withdrawn into a catheter device.

Several factors need to be considered in designing filters for use in the venous system. To prevent migration to the heart, the filter must be securely anchored to the adjacent vessel wall. However, filter anchoring must be accomplished in an atraumatic fashion so as to avoid vessel wall damage and perforation of the neighboring descending aorta and bowel. The area of contact with the vessel wall should be minimized in order to avoid vessel wall hypertrophy and caval stenosis. In addition, the filter must be capable of collapsing to an acceptable delivery profile to allow atraumatic intravascular delivery to the inferior vena cava. Additionally, the filter should direct blood clots away from the vessel wall to avoid vena cava thrombosis. Finally, it is preferred that such a filter device be removable from the implant site.

Three key shortcomings of current vena cava filter designs include: (1) inability or difficulty of filter removal, (2) non-optimal flow characteristics resulting in flow stasis, flow stagnation and filter occlusion and (3) caval stenosis. From a clinical perspective, there are many instances in which it would be desirable to place a venous filter in a patient on a prophylactic basis and then remove the filter when it is no longer required, e.g. young trauma patients, obese patients, or neurosurgical patients. In addition, current venous filters do not exhibit an optimized flow pattern in the presence of clot. It would be advantageous to develop a filter that distributes captured clot in such a way as to minimize significant central (mid-line, or about the longitudinal axis of the vessel) flow disturbances and avoid clot contacting the vessel wall. Finally, the hypertrophic tissue response in the regions of the vessel wall contacted by the filter device not only inhibits filter removal but also causes stenosis of the vena cava. This vessel stenosis can lead to thrombosis of the vena cava.

SUMMARY OF THE INVENTION

The present invention relates to a blood conduit filter (preferably a vena cava filter) that divides the transverse cross sectional area of a blood vessel (such as the inferior vena cava) into three annular regions or zones. The inner zone, the region immediately surrounding the longitudinal axis of the vessel, is maintained in a relatively open state with only minimal interference from the members making up the inner filter element (a clot deflector assembly) so that blood flow about the longitudinal axis (mid-line) of the vessel can be maintained substantially uninterrupted. Concentrically surrounding the inner zone is the intermediate zone, to which captured emboli are directed out of the bloodstream passing primarily through the inner zone. Finally, concentrically surrounding the intermediate zone is the outer zone adjacent to the vessel wall. This outer zone is intended to be maintained as a high flow region which is kept free of emboli. Emboli in the bloodstream immediately adjacent the vessel wall are directed away from the wall by the filter design and into the intermediate zone, thereby avoiding the accumulation of emboli adjacent the vessel wall that might otherwise lead to stenosis or stricture of the vessel.

The blood filter is intended primarily for use as a vena cava filter, although it can be made in a range of sizes allowing its use in vessels of various diameters. The filter is also preferably made to be removable with the use of flexible anchoring hooks.

The blood filter comprises multiple strut elements that extend outwardly and rearwardly from a center located along the longitudinal axis of the device. Preferably, some or all of the strut elements include an outwardly-directed flexible anchoring hook located some distance from the rearward end of the strut component.

Additionally, the device also includes a clot diverter component that includes multiple strut elements that also emanate from the device center. These diverter strut elements alternate radially around the device with the filter strut elements. They also extend outwardly and rearwardly from the center, but after reaching about half of the overall device maximum diameter, they turn back toward the longitudinal center line of the device and again converge at this longitudinal axis some distance rearward of the center from which they began. The clot diverter constructed in this fashion has elements spaced closely enough together to move clots outward from the longitudinal axis of the blood vessel and thus maintain this inner zone portion of the vessel open to blood flow.

The filter of the present invention is preferably made from a superelastic, highly flexible material such as nitinol. This material allows for strong and flexible struts and results in a device that may be easily compacted to a small diameter for insertion into a tubular delivery device such as a catheter tube. The filter device may be loaded into one end of a delivery catheter in either direction, depending on whether it is delivered distally or proximally to the implant site. When delivered to a desired site in the vasculature, the filter device is easily deployed by simply pushing it out of the end of the delivery catheter and allowing it to self-expand. It may be inserted into the vasculature at several different locations (e.g., a femoral vein, the right jugular vein or the subclavian vein).

The use of nitinol for the manufacture of the device allows for the device to be readily compacted for withdrawal from the vasculature into a retrieval catheter. The design of the struts results in a strong and non-evertable design, meaning that during retrieval the device is not everted back into itself but instead is collapsed diametrically and withdrawn into a catheter in the direction of the filter center component (i.e., in a proximal direction for a filter implanted in the venous system).

The filter device is most preferably made by cutting lengths of nitinol tubing, for example, by laser cutting. Devices constructed from a single nitinol tube, multiple tubes or combinations of tubes and wires might be used to implement the invention. Various other materials, alone or in combination including in combination with nitinol, may be used to construct these filter devices. These other materials may include, without limitation, various stainless steels and various polymeric materials including shape memory polymers.

A retrieval tool useful for retrieving the filter is also described; this tool can also be used for the retrieval or transport of various other devices. The design of the tool also allows it to be used as a temporary in vivo filter.

DETAILED DESCRIPTION OF THE DRAWINGS

Figure 1:
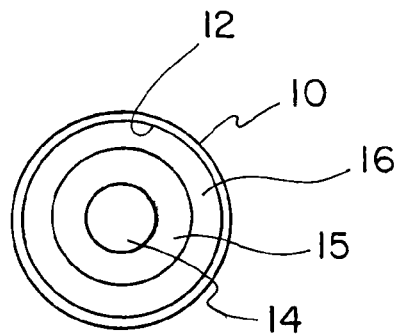
FIG. 1 is a schematic representation of a transverse view of a blood conduit indicating the three annular zones that blood flow is divided into by the blood filter of the present invention.

FIG. 1 is a schematic representation of a transverse view of a blood conduit 10 indicating the three annular zones 14, 15 and 16 that blood flow is divided into by the blood filter of the present invention. These are referred to respectively as the inner, intermediate and outer zones.

Figure 2:
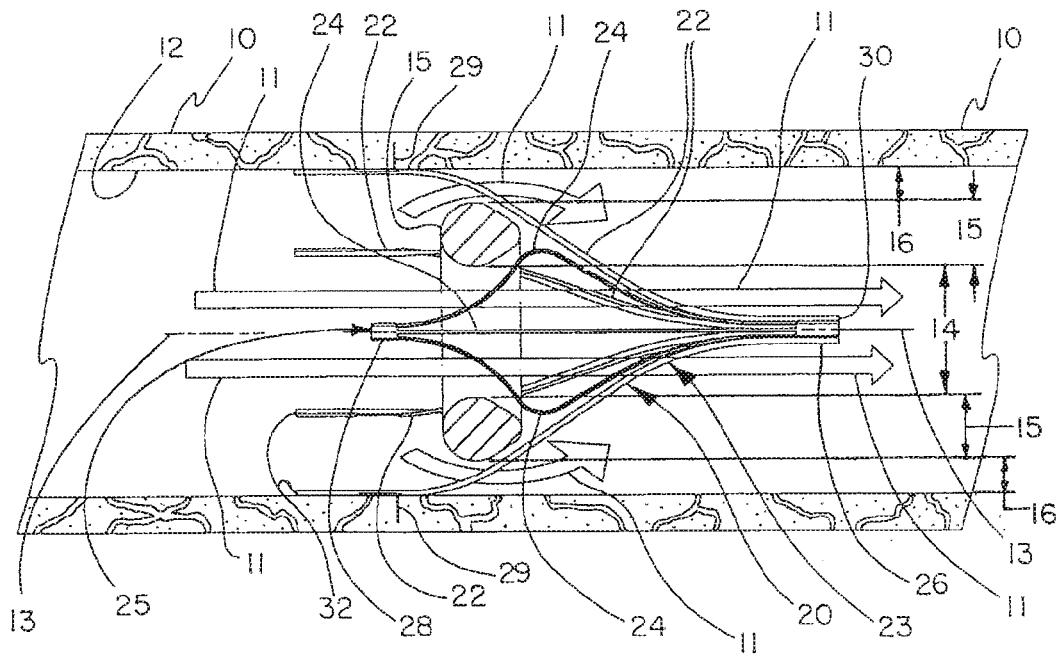
FIG. 2 is a side cross sectional view of the blood filter in use in a blood conduit.

FIG. 2 is a side cross sectional view of the blood filter 20 in use in a blood conduit 10. Filter 20 when implanted into a blood vessel 10 shares a common longitudinal axis 13 with the blood vessel 10. The filter 20 comprises multiple filter struts or filter elements 22 that emanate from the filter center 26. The filter struts 22 are made of wire-like materials, meaning that they are of small cross-section in comparison to their substantially greater lengths. This small cross-section may be round, elliptical, square, rectangular or otherwise as desired. For definition purposes, consistent with the use of the filter 20 in a venous application such as an inferior vena cava, filter center 26 is located at the proximal end 30 of the filter device 20, while the opposite end of the filter struts or filter elements 22 that emanate from the filter center 26 terminate at the distal end 32 of the filter 20.

Filter 20 further includes multiple clot deflector struts or elements 24 that also emanate from filter center 26. These clot deflector struts 24 alternate radially about the circumference of the filter device 20 with the filter struts 22. The clot deflector struts 24 extend outward radially only a portion of the inside diameter of the blood vessel 10 and then return to the filter device longitudinal axis 13 as they move rearwardly away from the filter center 26, until these clot deflector struts 24 again converge at the distal center 28, located along the longitudinal axis 13 some distance distally from filter center 26.

Blood flow in vessel 10 is indicated by arrows 11. Dimension arrows 14, 15 and 16 respectively define (as noted above for FIG. 1) the inner, intermediate and outer zones. It is seen how the combination of the filter struts 22 and clot deflector struts 24 allow blood flow in the inner zone 14 as the struts 24 of the clot deflector assembly 25 are sufficiently closely spaced to deflect blood clots of a size large enough to be of concern outwardly from this inner zone 14. The combined arrangement of clot deflector struts 24 and filter struts 22 result in accumulation of clot in intermediate zone 15, represented by toroidal shape 15 in FIG. 2. Filter struts 22 outside of the inner zone 14, in the region of the intermediate zone 15, are adequately close together to capture large blood clots as they are pushed in a proximal direction by blood flow. As these filter struts 22 extend distally and outwardly to contact the luminal surface 12 of vessel 10, they diverge sufficiently to loose their effectiveness as clot filters and define outer zone 16 by allowing blood to flow unimpeded through the outer zone 16.

Blood filter 20 is preferably anchored to the wall of vessel 10 by flexible anchoring hooks 29 as will be further described. These flexible anchoring hooks 29 are preferably located at some distance proximal to the distal end the filter strut 22 to which they are attached.

Figure 3:
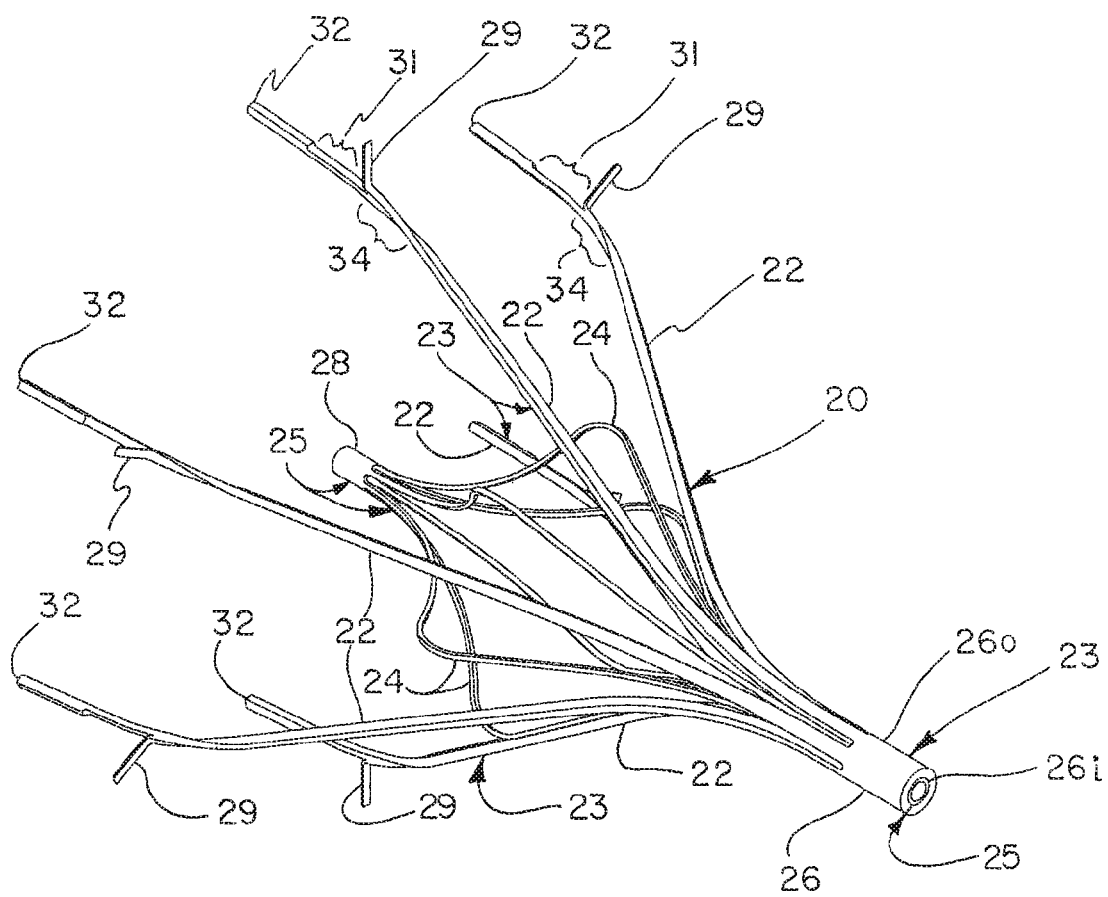
FIG. 3 is a perspective view of the blood filter of the present invention.
Figure 4:
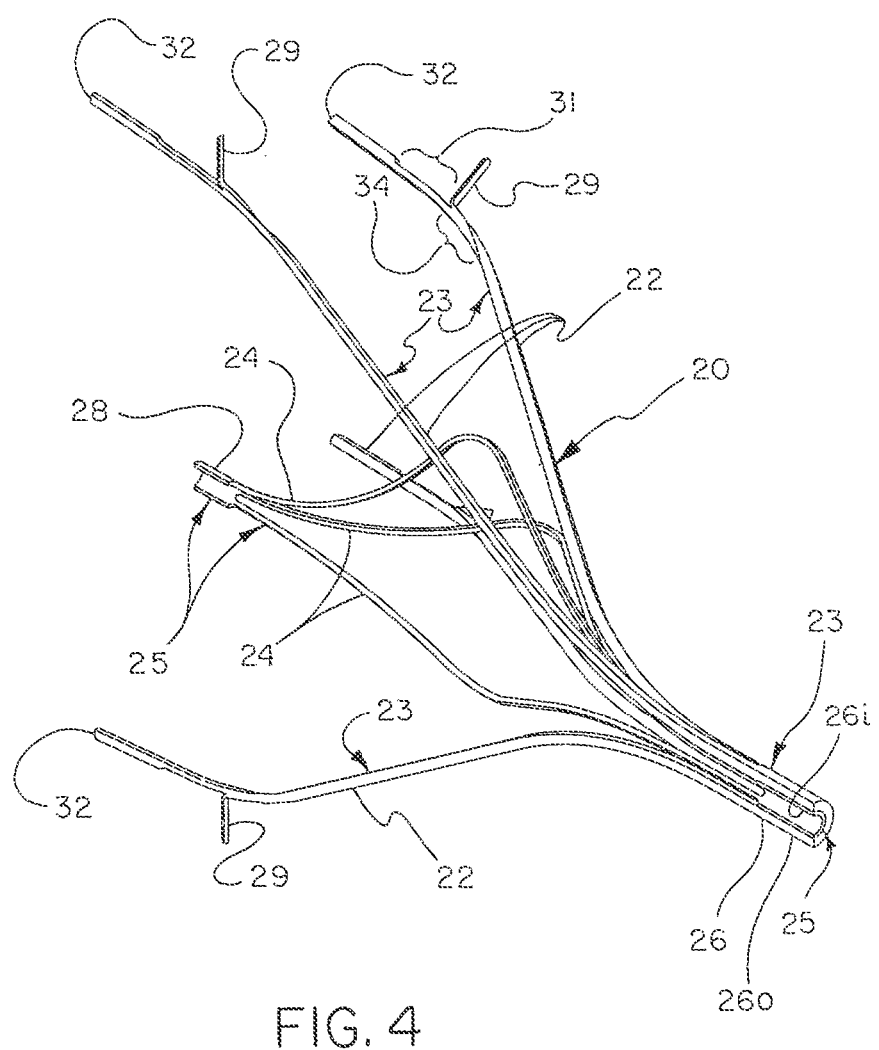
FIG. 4 is a perspective view of a longitudinal cross section of the blood filter of the present invention.

FIG. 3 is a perspective view of blood filter 20, while FIG. 4 is a longitudinal cross section of the perspective view of FIG. 3. These views describe a filter having six filter struts 22 alternating with six clot deflector struts 24. Flexible anchoring hooks 29 are shown in the preferred location some distance proximal to the distal end 32 of filter struts 22. It is apparent that a variety of filter anchoring hook arrangements are possible. Each filter strut 22 may be provided with one hook 29 as shown, or alternatively a pair of hooks 29 with one located on each side of filter strut 22. In another alternative, hooks 29 may be provided only on alternate filter struts 22, so that only three hooks 29 are provided for a filter 20 having six filter struts 22. In another alternative, when each filter strut 22 is provided with a pair of hooks 29, the pair of hooks 29 is located at a different distance from the distal end 32 than is the pair of hooks 29 of the adjacent filter struts 22. This allows the pairs of hooks 29 on adjacent filter struts 22 to be offset axially from each other and aids in allowing for a minimal filter diameter when the device is in a compacted state within a delivery catheter.

Hooks 29 are preferably located some distance proximal of the distal end 32 of filter struts 22. The base of a hook 29 may be located, for example, at a distance from distal end of about 1 mm, 1.5 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, 10 mm or greater. Not having the hook 29 located at the distal end 32 of a filter strut 22 avoids excessive penetration of hooks 29 into the vessel wall. Locating the hooks 29 as shown provides some length of filter strut 22 on either side of hook 29 and thereby provides supporting contact area of strut 22 on either side of hook 29 that prevents excessive penetration of hook 29 which could interfere with later retrievability of filter 20. This hook position also assures that contact with the vessel wall is maintained over a wide range of vessel diameters. It is further noted that the distal ends 32 of filter struts 22 may optionally be flattened to provide greater width and surface area at distal end 32. Likewise, the distal ends 32 (flattened or not) may be provided with radiopaque plating or radiopaque inserts to enhance visualization of filter 20 during and following implantation.

Figure 5:
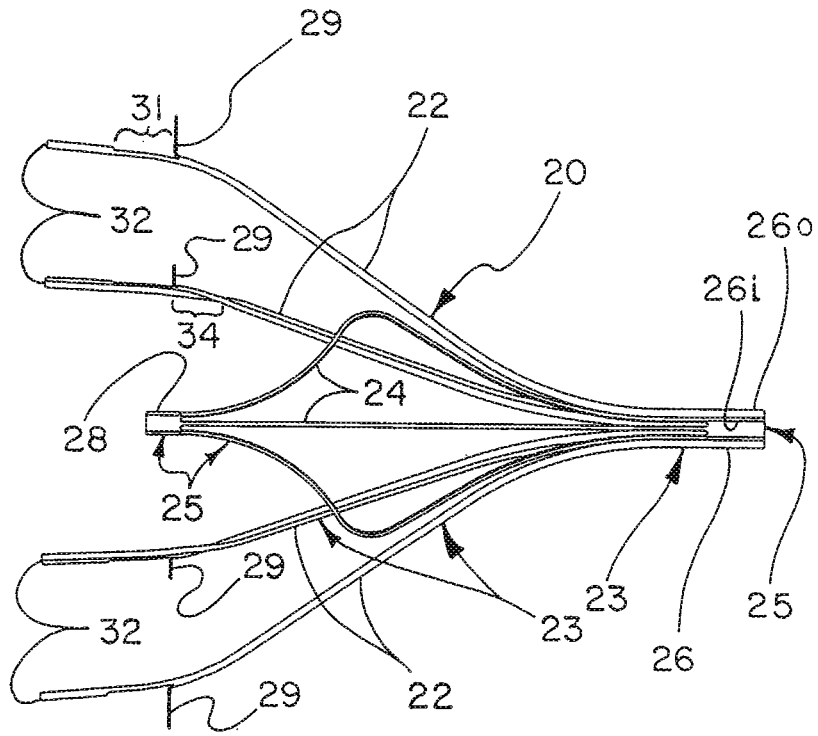
FIG. 5 is a side view of the longitudinal cross section of the blood filter of the present invention.

The longitudinal cross section of the perspective view of FIG. 4 and the longitudinal cross sectional side view of FIG. 5 show how the filter device 20 may be made from two nitinol tubes. The filter struts 22 emanate from a common length of tubing, the filter center 26, here designated 26o as the outer tubular portion of the filter center 26. The inner filter center 26i is the common point from which the clot deflector struts 24 emanate. These clot deflector struts 24 re-converge at the distal center 28. It is apparent how the clot deflector assembly 25 is made by longitudinally cutting through the wall of a length of tubing at a number of evenly spaced intervals that corresponds with the number of intended clot deflector struts 24. The ends of the tubing are left uncut to create filter center 26i and distal center 28. Cutting may be accomplished by various known means including laser cutting. A suitable nitinol tubing for clot deflector assembly 25 intended for use with filter strut assembly 23 described further below has an outside diameter of about 1.3 mm and a wall thickness of about 0.2 mm. Six lengthwise cuts through the wall of this tubing provide clot deflector struts 24 of about 0.2 mm width. Following cutting, the individual clot deflector struts 24 are bent outwardly from the position they held in the precursor tube by the application of axial compression to the lengthwise cut tube.

The filter struts 22 may be cut (e.g., laser cut) from an outer tube, of which only one tubular end remains after cutting, at filter center 26o (which, as shown is an outer tube that fits tightly and concentrically around one end of the inner tube forming the clot deflector struts at 26i). A preferred way of manufacturing this filter strut component allows the making of a pair of filter strut assemblies 23, wherein a length of tubing sufficiently long to make two filter strut assemblies 23 is used. A suitable nitinol tubing (for example) is of 2.2 mm diameter with a 0.35 mm wall thickness. A sufficient length is left at each end of this length of tubing to provide a filter center 26o at each end. The length between these two ends is then cut longitudinally through the wall of the tubing at (for example) six evenly spaced intervals (i.e., at 60 degree intervals around the circumference of the tube for six filter struts; using the tubing described above cut into six struts results in a strut width of about 0.45 mm). When these longitudinal cuts are complete, the lengthwise cut tubing is cut in half transversely at the mid-point of the length to provide two filter strut assemblies 23; the transverse cut becomes the distal end 32 of each of the two resulting filter strut assemblies 23. Following the transverse cutting step, the individual filter struts 22 are bent outwardly from the position they held previously in the precursor tube to a shape as desired for use as the filter strut assembly 23 of the blood filter 20. One method of accomplishing this is to force the transversely cut end against the point of a conical form, thereby flaring the struts outward.

FIGS. 3-5 also show a preferred method of providing anchoring hooks 29. As shown, the hooks 29 are made by cutting through the thickness of a strut 22 at the intended location for hook 29 (region 31). This cut is made in the same direction as the previous cuts made through the precursor tube wall to create the filter struts 22. The cut is begun transversely into the width of the strut 22 to a dimension equal to the desired thickness of hook 29. When the cut is sufficiently deep into the width of strut 22, the cut turns 90 degrees and continues parallel to the length of the strut 22 for a distance equal to the desired length of hook 29, at which point the cut is complete. The strut 22 is then twisted axially 90 degrees in region 34 so that the cut surface of the strut 22 (region 31) faces outwardly as necessary to contact the luminal surface 12 of a vessel wall. The thin segment of material resulting from the cut is then bent upward so that its free end, the point of hook 29, is directed outwardly as shown to face a vessel wall. The base of hook 29 remains integral with the material of filter strut 22. The resulting hook 29 is flexible and offers adequate anchoring without substantially interfering with subsequent removability of the filter 20.

Other angular orientations for hooks 29 (other than about 90 degrees to filter strut 22) may also prove advantageous. For example, it is possible to fold hook 29 back on itself to the extent that it is pointing proximally or at some desired angle between a proximal direction and 90 degrees to the strut. Likewise, the hook 29 may be provided to point distally if desired.

While further shaping of the pointed tip of anchor hooks 29 is not required, hooks 29 may be modified to any configuration desired by a variety of known metal forming techniques. One such method involves simply cutting the tip at any desired angle with cutting pliers to create a sharp point at the tip of hook 29.

After the filter strut assembly 23 and the clot deflector assembly 25 are fitted concentrically together at the filter center 26, they are permanently joined together to create essentially a one-piece filter device by a suitable method such as by welding. Welding together of the inner 26i and outer 26o filter center tubes may be accomplished at the proximal tip of the filter 20 where the ends of both tubes 26o and 26i are exposed.

The filter device is heat treated as necessary following forming steps. The filter strut assembly 23 and clot deflector assembly 25 may be separately heat treated prior to being welded together as it is believed that the subsequent welding will not adversely affect the previous heat treatment. A preferred nitinol heat treatment results in an $A_f$ of 37° C.

Figure 6:
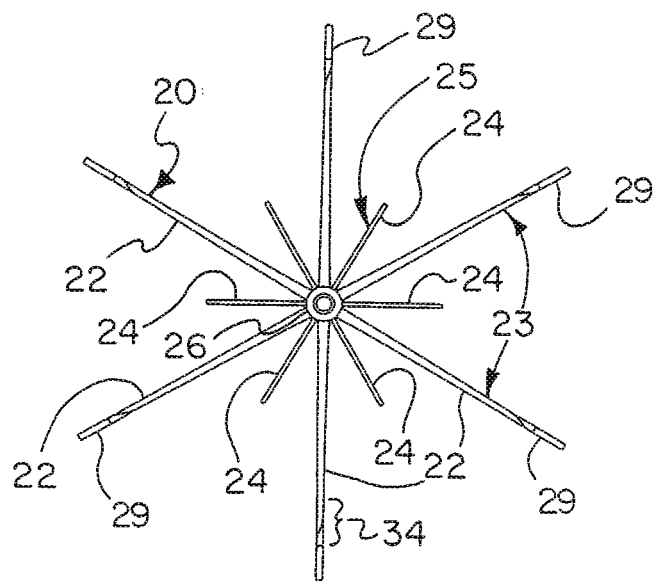
FIG. 6 is an end view of the blood filter of the present invention.

FIG. 6 is a proximal end view (i.e., looking in a distal direction) of the blood filter 20 that further describes the above-mentioned aspects.

It is also noted that all surfaces or selected surfaces of blood filter 20 may be beneficially provided with coatings of various types, including bioabsorbable coatings. Coatings, for example, may allow for the delivery of various drugs to the adjacent tissues. This could aid in minimizing the tissue response and resulting tissue overgrowth of the struts. Examples of useful coatings are described in WO 02/026281 and WO 2004/012783.

Figure 7A:
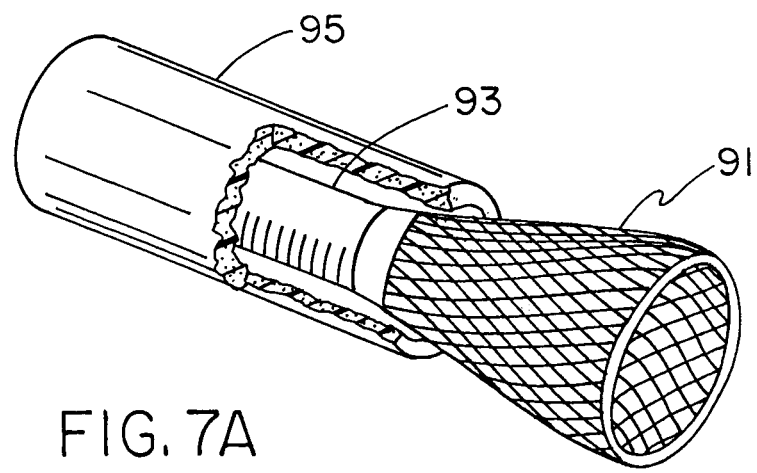
FIGS. 7A and 7B describe a snare type retrieval tool intended to allow removal of the blood filter.
Figure 7B:
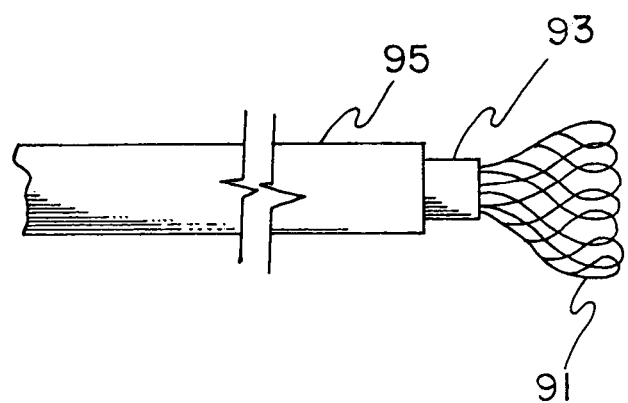

Coaxial catheters may be used to effect retrieval of devices of various types including blood filters of the present invention, as shown by the perspective view of the catheter delivery and retrieval system illustrated by FIGS. 7A and 7B. A funnel-shaped wire mesh snare 91 is provided affixed to the distal end of a first catheter 93, which is delivered to the retrieval site by an outer, coaxial catheter 95. Extending the inner catheter 93 beyond the distal end of the outer catheter 95 allows the snare 91 to be deployed, allowing its distal end to self-expand to a larger diameter at which it may be used to capture a device such as blood filter 20. Withdrawing inner catheter 93 back into outer catheter 95 forces snare 91 back to a smaller diameter, thereby retaining a captured device within snare 91. This snare 91 may also be included as a portion of the catheter delivery system enabling acute retrieval of a filter device 20 if that should be desired at a time following deployment of device 20.

Snare 91 may be made of a variety of filamentary materials; superelastic nitinol wire is preferred for the self-expanding characteristic desired for best performance of snare 91. The snare 91 may be of woven or braided construction, but may also be made using a filament winding method. The filament used to make the snare may optionally be provided with a coating or covering material over the surface of the filament (e.g., ePTFE tape helically wrapped over the filament surface). Likewise, snare 91 may also be provided with a covering (e.g., ePTFE film) in the fashion of a covering over a stent to achieve a stent-graft.

Figure 8A:
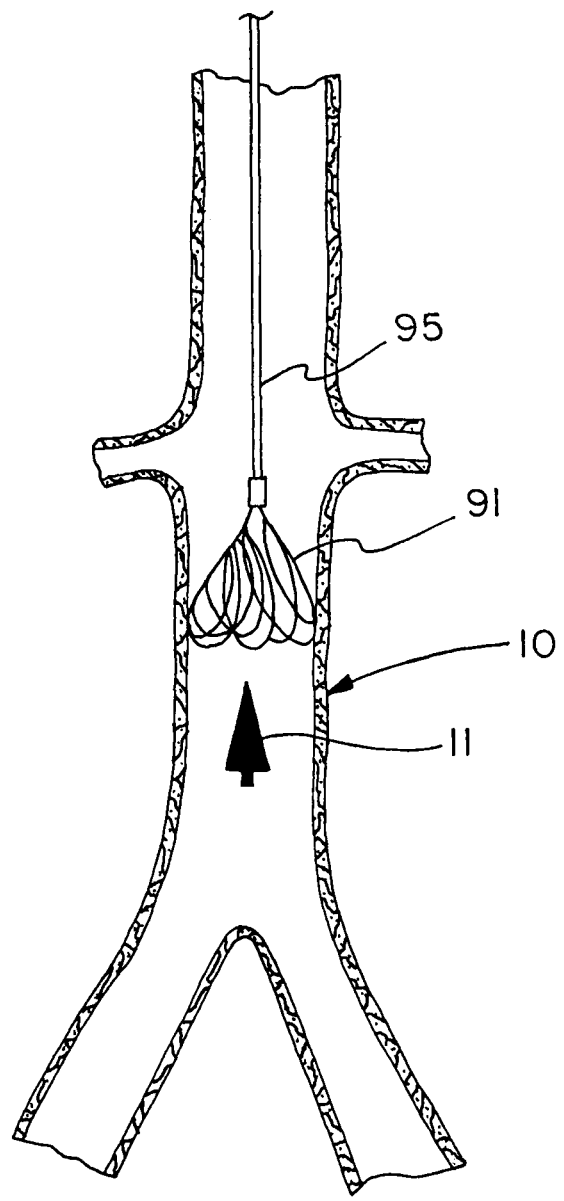
FIGS. 8A and 8B show the use of the snare type retrieval tool as a temporary blood filter.
Figure 8B:
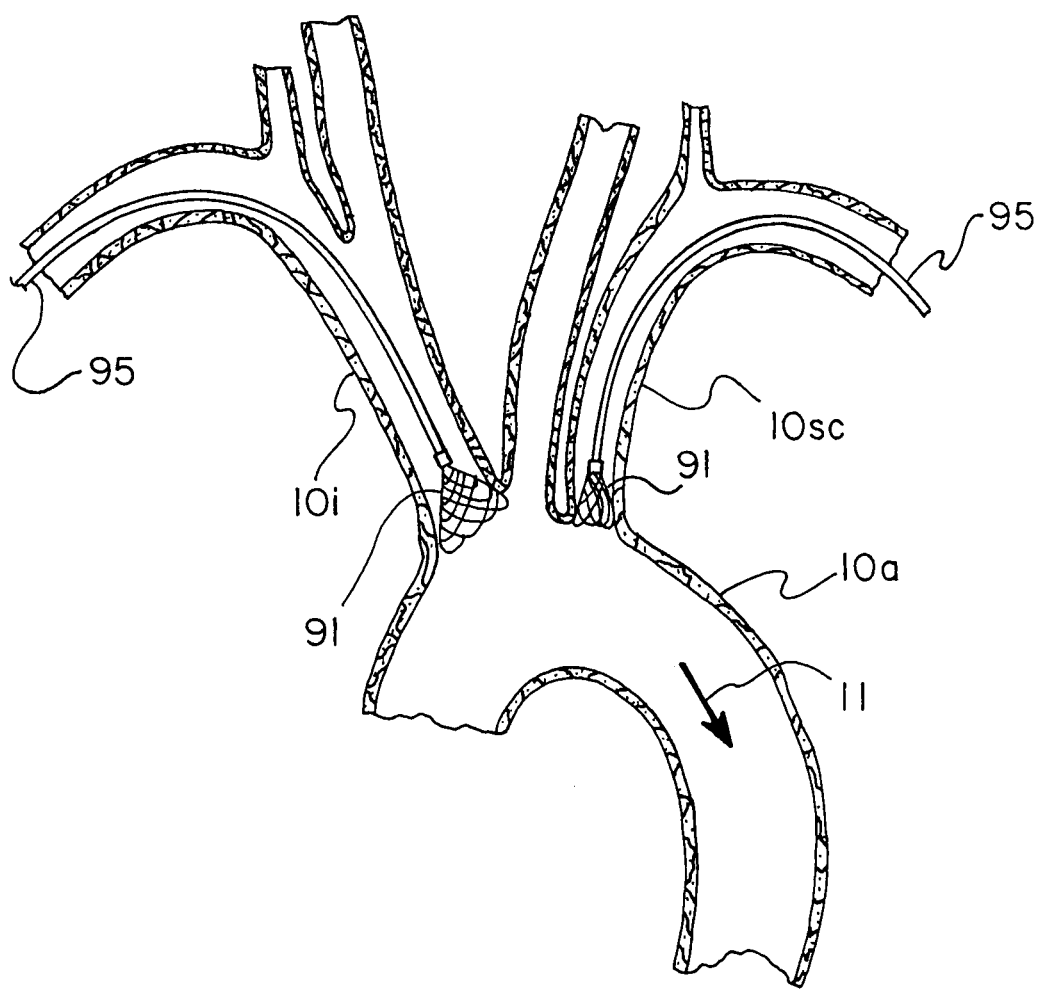

Snare devices 91 of this type may be desirably used as temporary venous filters. FIG. 8A shows such a snare 91 used as a temporary inferior vena cava filter with a delivery catheter 95 serving as a temporary indwelling catheter. FIG. 8B shows snare devices 91 of this type used as temporary filters in the inominate 10i and subclavian 10sc arteries during surgery involving the aortic arch 10a.

Figure 9A:
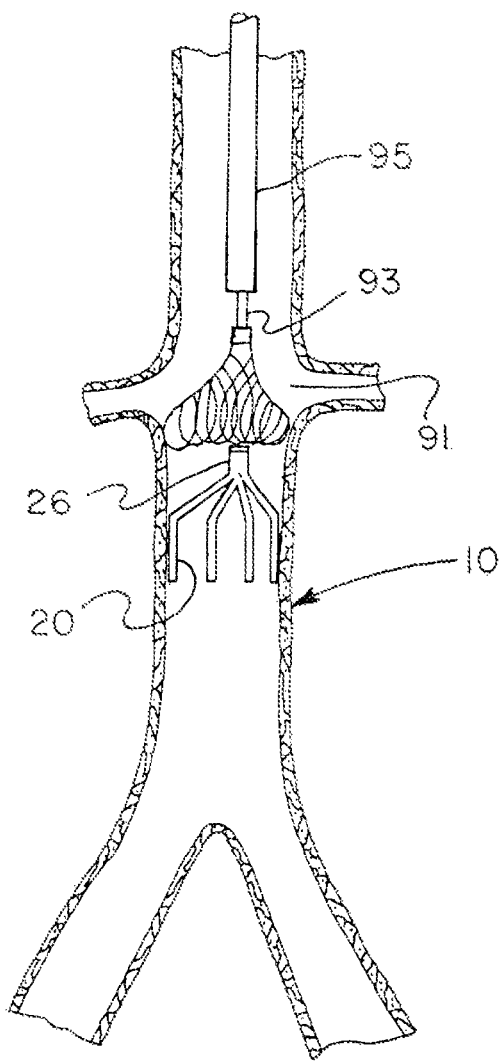
FIGS. 9A-9C show the use of the snare type retrieval tool to remove an implanted blood filter.
Figure 9B:
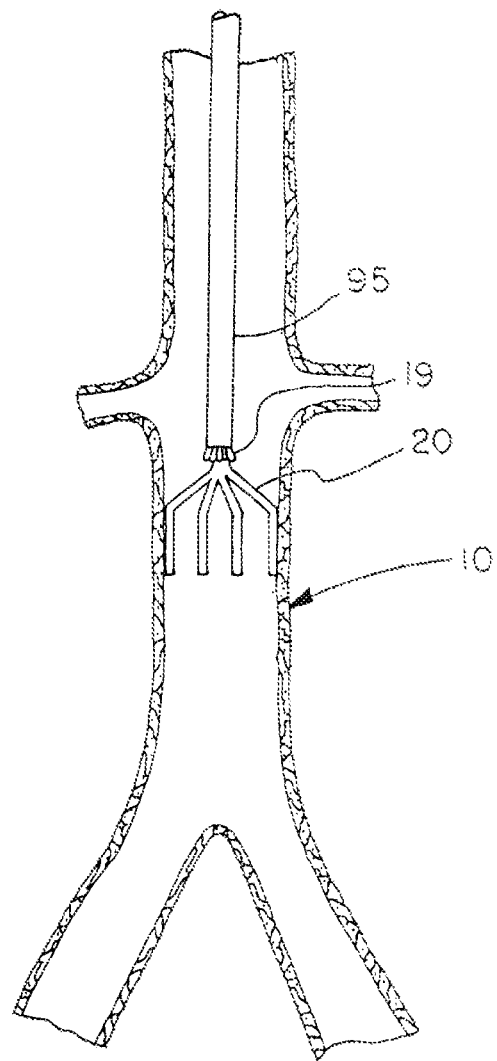
Figure 9C:
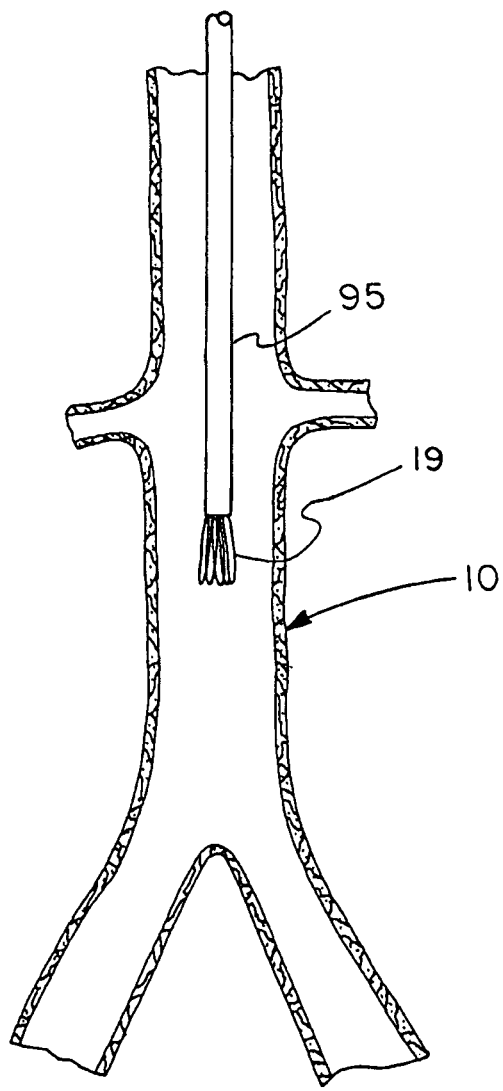

FIG. 9A shows a snare device 91 positioned to retrieve a removable blood filter 20. Catheter 95 is inserted into the vasculature via a suitable access point and moved into appropriate position to effect the retrieval. Snare 91 is extended from catheter 95 until it is positioned about the filter center 26. Catheter 95 is moved distally while catheter 93 is maintained in position to hold the mouth of snare 91 about filter center 26; distal movement of catheter 95 with respect to catheter 93 causes snare 91 to be drawn into catheter 95 and results in closing of snare 91 about filter center 26 as shown by FIG. 9B. FIG. 9C shows how continued distal movement of catheter 95 with respect to catheter 93 continues further withdrawal of snare 91 into catheter 95 while snare 91 retains its grip on filter center 26, resulting in filter 20 also being diametrically collapsed and withdrawn into catheter 95. When filter 20 is fully collapsed and withdrawn into catheter 95, catheter 95 may be withdrawn from the vasculature along with filter 20.

While particular embodiments of the present invention have been illustrated and described herein, the present invention should not be limited to such illustrations and descriptions. It should be apparent that changes and modifications may be incorporated and embodied as part of the present invention within the scope of the following claims.

We claim:

1. A blood filter adapted for deployment in a blood vessel having a wall, comprising a non-everting filter frame having a longitudinal axis and having at least a first outer zone, a second intermediate zone and a third inner zone, the first, second and third zones in annular relationship with each other and disposed about the longitudinal axis, the first, outer zone adjacent to the wall of the blood vessel, the second, intermediate zone adapted for collection of blood clots, and the third, inner zone allowing for continuing blood flow through the filter substantially uninterrupted by blood clots collected in the intermediate zone, wherein said filter frame further comprises a filter center located on the longitudinal axis at a proximal end of the filter and multiple filter struts extending radially outward from the filter center in a distal direction of a length sufficient to allow distal ends of said filter struts to contact the wall of said blood vessel, said filter struts being spaced circumferentially apart from each other, and also having multiple clot deflector struts that also extend radially outward from the filter center in a distal direction for a distance insufficient to allow them to contact the wall of said blood vessel, said clot deflector struts being spaced circumferentially apart from each other and located circumferentially between pairs of adjacent filter struts, wherein distal ends of said clot deflector struts return to a distal center located on said longitudinal axis a distance distally from said filter center.

2. The blood filter according to claim 1 wherein the multiple filter struts are arranged to form a substantially conical shape.

3. The blood filter according to claim 1 wherein the inner zone is defined by the clot deflector struts arranged to have a substantially conical shape.

4. The blood filter according to claim 1 wherein the inner zone is defined by said clot deflector struts collectively arranged to form an assembly having opposing ends of substantially smaller diameter than a middle region between the opposing ends.

5. The blood filter according to claim 1 wherein the filter comprises wire-like filter elements.

6. The blood filter according to claim 1 wherein the filter does not occlude blood flow therethrough.

7. The blood filter according to claim 1 wherein at least a portion of the filter frame comprises nitinol.

8. The blood filter according to claim 1 wherein the filter is configured for use as a vena cava filter.

9. The blood filter according to claim 1 wherein the filter consists of two pieces.

10. The blood filter according to claim 1 wherein the filter has a smaller compacted diameter for insertion into and passage through a first portion of a body conduit and a larger expanded diameter for location of the filter within a second portion of the body conduit.

11. The blood filter according to claim 1 wherein the filter is removable from a body conduit at a time subsequent to implantation within the body conduit.

* * * * *